United States Patent
Miyata et al.

(10) Patent No.: US 7,462,266 B2
(45) Date of Patent: *Dec. 9, 2008

(54) APPARATUS FOR DETECTING CONCENTRATION OF NITROGEN OXIDE

(75) Inventors: Shigeru Miyata, Aichi (JP); Noriaki Kondo, Aichi (JP); Hiroshi Inagaki, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 380 days.

This patent is subject to a terminal disclaimer.

(21) Appl. No.: 10/329,489

(22) Filed: Dec. 27, 2002

(65) Prior Publication Data

US 2003/0106808 A1    Jun. 12, 2003

Related U.S. Application Data

(62) Division of application No. 09/737,771, filed on Dec. 18, 2000, now Pat. No. 6,533,921, which is a division of application No. 09/022,208, filed on Feb. 11, 1998, now Pat. No. 6,228,252.

(30) Foreign Application Priority Data

Feb. 13, 1997 (JP) ................................. 9-28971

(51) Int. Cl.
*G01N 27/407* (2006.01)
(52) U.S. Cl. .................... 204/408; 204/425; 205/781
(58) Field of Classification Search ........... 205/781, 205/784.5, 785; 204/408, 425, 426
See application file for complete search history.

(56) References Cited

U.S. PATENT DOCUMENTS

| | | |
|---|---|---|
| 4,543,176 A | 9/1985 | Harada et al. |
| 4,722,779 A | 2/1988 | Yamada et al. |
| 4,851,103 A | 7/1989 | Usami et al. |
| 4,875,990 A | 10/1989 | Kodachi et al. |
| 4,909,072 A | 3/1990 | Logothetis et al. |

(Continued)

FOREIGN PATENT DOCUMENTS

EP    0 117 692 A    9/1984

(Continued)

OTHER PUBLICATIONS

960334, Copyright 1996, Society of Automotive Engineers, Inc., "Thick Film ZrO2 NOx Sensor," by Nobuhide Kato, Kunihiko Nakagaki and Noriyuki Ina, pp. 137-142.
European Search Report for European Application No. 98102452.4-2204.

*Primary Examiner*—Kaj K Olsen
(74) *Attorney, Agent, or Firm*—Morrison & Foerster LLP

(57) ABSTRACT

Apparatus for detecting the NOx concentration includes a first measurement chamber 20 communicating with the gas under measurement via a diffusion rate defining layer 4d and a second measurement chamber 26 communicating with the first measurement chamber 20 via diffusion limiting layers 6d, 22d. A first pump current IP1 is controlled so that an output of a Vs cell 6 will be equal to the reference voltage VCO for controlling the oxygen concentration in the first measurement chamber 20 to a pre-set low value. A constant voltage is applied across the second pump cell 8 for decomposing the NOx component in the second measurement chamber 26 for pumping out oxygen for detecting the NOx concentration from a second pump current IP2. The sensor temperature is detected from the internal resistance of the Vs cell for controlling the current supplied to the heaters 12, 14. If the temperature of the gas under measurement is changed rapidly, the sensor temperature is changed. The detected second pump current IP2 is corrected depending on an offset of the detected sensor temperature from the target temperature assuring detection of the NOx concentration to high accuracy.

4 Claims, 7 Drawing Sheets

U.S. PATENT DOCUMENTS

| | | | |
|---|---|---|---|
| 5,145,566 A | 9/1992 | Logothetis et al. | |
| 5,288,389 A | 2/1994 | Yamada et al. | |
| 5,413,683 A | 5/1995 | Murase et al. | |
| 5,700,367 A | 12/1997 | Yamada et al. | |
| 5,763,763 A | 6/1998 | Kato et al. | |
| 5,780,710 A | 7/1998 | Murase et al. | |
| 5,833,836 A | 11/1998 | Takami et al. | |

FOREIGN PATENT DOCUMENTS

| | | |
|---|---|---|
| EP | 0 678 740 A | 10/1995 |
| JP | 59-163556 | 9/1984 |
| JP | 63-38154 | 2/1988 |
| JP | 2-122255 | 5/1990 |
| JP | 6-18480 | 1/1994 |
| JP | 6-27078 | 2/1994 |
| JP | 8-29387 | 2/1996 |
| JP | 8-271476 | 10/1996 |
| JP | 10-123094 | 5/1998 |
| JP | 10-142194 | 5/1998 |
| JP | 10-185868 | 7/1998 |
| JP | 10-227760 | 8/1998 |
| JP | 10-232220 | 9/1998 |
| WO | 30146 | 11/1995 |

APPARATUS FOR DETECTING CONCENTRATION OF NITROGEN OXIDE

This application is a divisional of Ser. No. 09/737,771 filed Dec. 18, 2000, now U.S. Pat. No. 6,533,921 issued Mar. 18, 2002, which is a division of Ser. No. 09/022,208 filed Feb. 11, 1998, now U.S. Pat. No. 6,228,252, issued May 8, 2001.

TECHNICAL FIELD OF THE INVENTION

This invention relates to an apparatus and method for detecting the concentration of nitrogen oxide as harmful components discharged from a variety of combustion devices, such as internal combustion engines.

BACKGROUND OF THE INVENTION

Following discussions are given on the related art in the light of the present invention.

Up to now, there has been known an apparatus for detecting the concentration of nitrogen oxide in which, as disclosed for example in European Patent Publication 0678740A1, SAE paper No. 960334 p. 137 to 142, 1996, a first measurement chamber communicating via a first diffusion rate defining layer with a gas to be measured and a second measurement chamber communicating via second diffusion rate defining layer with this first measurement chamber are formed by an oxygen ion conducting electrolyte layer, a first oxygen pumping cell and an oxygen concentration measurement cell are formed in the first measurement chamber by sandwiching a solid electrolyte layer between porous electrodes and, and in which a second oxygen pumping cell and an oxygen concentration measurement cell are formed in the second measurement chamber by sandwiching a solid electrolyte layer between porous electrodes, to constitute a sensor for detecting the concentration of nitrogen oxides (NOx) in the exhaust gases of the internal combustion engines.

In this type of the nitrogen oxide concentration detecting apparatus, the current is supplied to the first oxygen pumping cell so that the output voltage from the oxygen concentration measurement cell will be at a pre-set constant value and oxygen is pumped out from the first measurement chamber to control the oxygen concentration to a constant value. A constant voltage is applied across the second oxygen pumping cell for further pumping oxygen out of the second measurement chamber. The NOx concentration in the gas under measurement is detected from the value of the current flowing in this second measurement chamber.

In the exhaust gases from the internal combustion engines, that is gases under measurement, there are gaseous components other than NOx, namely oxygen, carbon monoxide or carbon dioxide etc. In the above-mentioned the nitrogen oxide concentration detecting apparatus, the current is caused to flow in the first oxygen pumping cell for extracting oxygen in the first measurement chamber, substantially in its entirety, and a constant voltage is applied across the second oxygen pumping cell in the second measurement chamber in a direction of pumping out oxygen out of the second measurement chamber, to decompose NOx in the gas under measurement into nitrogen and oxygen by the catalytic action of the porous electrode constituting the second oxygen pumping cell, to extract oxygen from the second measurement chamber. This enables detection of the NOx concentration in the gas under measurement without being affected by the gaseous components contained in the gas under measurement.

Also, in this type of the nitrogen oxide concentration detecting apparatus, it is necessary to heat the sensor to a pre-set activation temperature, e.g., not less than 800° C., for correctly measuring the NOx concentration by the above-described detection method. Thus, a heater is separately provided for heating the sensor.

For controlling the sensor to a pre-set temperature using the heater, it may be contemplated to use a control method customarily used in an oxygen sensor configured for detecting the oxygen concentration in the exhaust gases using an oxygen concentration sensor comprised of a solid electrolyte layer sandwiched between porous electrodes.

That is, for controlling the sensor temperature, a variety of methods have been devised, such as a method controlling the amount of the current supplied to the heater so that the heat evolution in the heater will be constant, a method controlling the amount of the heater current by a pre-set control pattern so that the sensor temperature will be a target temperature, or a method of detecting the sensor temperature for controlling the amount of the current supplied to the heater, as disclosed in JP Patent Kokai JP-A-59-163556 or in JP Patent Kokai JP-A-59-214756. It may be envisaged to use these conventional control methods in the nitrogen oxide concentration detecting apparatus.

SUMMARY OF THE DISCLOSURE

However, in the course of the investigations toward the present invention, certain problems have been encountered. That is in distinction from an oxygen sensor, the nitrogen oxide concentration detecting apparatus includes three cells in the sensor. Moreover, since it is difficult to provide a heater in each cell to control its temperature, there is posed a problem of how to apply the above-mentioned control methods.

In the nitrogen oxide concentration detecting apparatus, in particular, if the sensor temperature is changed, the oxygen concentration in the first measurement chamber, controlled by the current allowed to flow in the first oxygen pumping cell, and hence the oxygen concentration in the second measurement chamber, are varied, thus significantly varying the results of detection of the NOx concentration. Thus, for assuring detection accuracy of the NOx concentration, it is demanded that temperature control can be executed efficiently by a simplified structure so that the oxygen concentration in the first measurement chamber is not varied by changes in the sensor temperature. Up to now, a temperature controlling method capable of sufficiently meeting to this request has not been established, such that a nitrogen oxide concentration detection device which has realized temperature characteristics by a simplified structure has not been put to practical use.

Also, the nitrogen oxide concentration detection device suffers from a defect that, since the detected results are varied significantly by changes in the sensor temperature, the results of detection can be affected by changes in temperature of the gas being measured, such that, if the sensor temperature can be controlled accurately, the results of detection tend to be momentarily fluctuated during the transient period when the temperature of the gas being measured is changed.

In view of the above problems, it is a primary object of the present invention to provide a novel nitrogen oxide concentration detection apparatus (or method) capable of efficiently controlling the sensor temperature such as to prevent the results of detection of the NOx concentration from being varied.

It is a second object of the present invention to provide a novel nitrogen oxide concentration detection apparatus (or method) for correcting NOx concentration detection errors accompanying temperature changes of the gas under measurement that cannot be controlled by this temperature control.

Further objects of the present invention will become apparent in the entire disclosure.

According to a first aspect of the present invention, there is provided a nitrogen oxide concentration detection apparatus generally including a main body portion of a sensor having a first measurement chamber and a second measurement chamber. The first measurement chamber has a first oxygen pumping cell and an oxygen concentration measurement cell, the first oxygen pumping cell being made up of an oxygen ion conducting solid electrolyte layer sandwiched between porous electrodes. The first measurement chamber communicates via a first diffusion rate defining layer with a gas under measurement. The second measurement chamber is made up of an oxygen ion conducting solid electrolyte layer sandwiched between porous electrodes, and communicates with the first measurement chamber via a second diffusion rate defining layer. The nitrogen oxide concentration detection apparatus also includes pump current controlling means for pumping out oxygen from the first measurement chamber by the first oxygen pumping cell so that an output voltage of the oxygen concentration measurement cell will be constant, for thereby controlling the oxygen concentration in the first measurement chamber to a constant value. The nitrogen oxide concentration detection apparatus also includes constant voltage applying means for applying a constant voltage to the second oxygen pumping cell in a direction of pumping out oxygen from the second oxygen pumping cell, nitrogen oxide concentration detection means for detecting the concentration of nitrogen oxides in the gas under measurement based on the current value flowing in the second oxygen pumping cell on application of the constant voltage and a heater for heating the main body portion of the sensor to a temperature capable of detecting the nitrogen oxide concentration.

As characteristic of the present invention, the nitrogen oxide concentration detection apparatus further includes temperature detection means for detecting the temperature of the oxygen concentration measurement cell and heater current controlling means for controlling the current supply to the heater so that the temperature of the oxygen concentration measurement cell detected by the temperature detection means will be a pre-set target temperature.

According to a second aspect, the nitrogen oxide concentration detection apparatus further includes correction means for correcting the concentration of nitrogen oxide as detected by the nitrogen oxide concentration detection means depending on deviation from the target temperature of the temperature of the oxygen concentration measurement cell detected by the temperature detection means to temperature-compensate a detected value of the concentration of nitrogen oxides.

According to a further aspect, there is provided a novel method for detecting concentration of nitrogen oxide.

The method comprises various steps:

(a) providing a sensor having a first measurement chamber and a second measurement chamber, said first measurement chamber including a first oxygen pumping cell and an oxygen concentration measurement cell, said first measurement chamber communicating via a first diffusion rate defining layer with a gas under measurement, said second measurement chamber communicating with said first measurement chamber via a second diffusion rate defining layer;

(b) controlling pump current for pumping out oxygen from the first measurement chamber by the first oxygen pumping cell to control the oxygen concentration in the first measurement chamber;

(c) applying a voltage to the second oxygen pumping cell for pumping out oxygen from the second oxygen pumping cell;

(d) detecting the concentration of nitrogen oxides in the gas under measurement based on the current value flowing in the second oxygen pumping cell; and (e) heating the sensor to a temperature capable of detecting the nitrogen oxide concentration;

The method further comprises the steps of:

(f) detecting the temperature of the oxygen concentration measurement cell; and (g) controlling the temperature of the oxygen concentration measurement cell based on said temperature to a pre-set target temperature.

In the method, the concentration of nitrogen oxide as detected by step (d) is corrected depending on deviation from said target temperature of the temperature of the oxygen concentration measurement cell detected by step (f) to temperature-compensate a detected value of the concentration of nitrogen oxides.

The method comprises further features which will become apparent in the entire disclosure and claims.

PREFERRED EMBODIMENTS OF THE INVENTION

The nitrogen oxide concentration detection apparatus detects the NOx concentration using a main body portion of the sensor having a first measurement chamber and a second measurement chamber. The first measurement chamber includes a first oxygen pumping cell and an oxygen concentration measurement cell. The first oxygen pumping cell is made up of an oxygen ion conducting solid electrolyte layer sandwiched between porous electrodes. The first measurement chamber communicates via a first diffusion rate defining layer with a gas under measurement. The second measurement chamber is made up of an oxygen ion conducting solid electrolyte layer sandwiched between porous electrodes, the second measurement chamber communicating with the first measurement chamber via a second diffusion rate defining layer. The pump current control means pumps out oxygen from the first measurement chamber by the first oxygen pumping cell so that an output voltage of the oxygen concentration measurement cell will be at a pre-set constant value for thereby controlling the oxygen concentration in the first measurement chamber to a constant value. The constant voltage applying means applies a constant voltage across the first oxygen pumping cell in a direction of pumping out oxygen from the first measurement chamber for controlling the oxygen concentration in the first measurement chamber to a constant value. The nitrogen oxide concentration detection means detects the NOx concentration in the gas under measurement based on the value of the current flowing in the second oxygen pumping cell on application of the constant voltage.

In the nitrogen oxide concentration detection device of the present invention, a heater for heating the main body portion of the sensor to a temperature capable of detecting the NOx concentration is provided as in the conventional device. The current supply to this heater is controlled by the heater current supply control means so that the temperature of the oxygen concentration measurement cell detected by the temperature detection means will be equal to a pre-set target temperature.

Thus, with the nitrogen oxide concentration detect ion apparatus of the present invention, it is possible to correctly detect the oxygen concentration in the first measurement chamber most significantly influencing the NOx concentration by the oxygen concentration measurement cell. Also, if, as in the present invention, the temperature of the oxygen concentration measurement cell is controlled to the target temperature by the heater, the temperature of the first oxygen pumping cell and the second oxygen pumping cell can be controlled to substantially a constant value. The result is that, according to the present invention, the oxygen concentration in the first measurement chamber can be controlled to a constant concentration by controlling the current supply to the first oxygen pumping cell by the pump current control means, thus enabling correct detection of the NOx concentration in the gas under measurement from the current flowing in the second oxygen pumping cell.

In the nitrogen oxide concentration detection apparatus of the present invention, the amount of the current flowing to the heater for heating the main body portion of the sensor is controlled so that the temperature in the oxygen concentration measurement cell for detecting the oxygen concentration in the first measurement chamber most strongly influencing the NOx concentration detection accuracy will be equal to the target temperature for correctly detecting the NOx concentration without being affected by changes in temperature of the main body portion of the sensor. Since the temperature control system for the main body portion of the sensor can be constituted simply by providing temperature detection means for detecting the temperature of the oxygen concentration measurement cell and heater current supply control means for controlling current supply to the heater, the nitrogen oxide concentration detection device of the present invention can perform temperature control of the main body portion of the sensor efficiently by a simplified structure.

In the nitrogen oxide concentration detection apparatus according to the second aspect, correction means corrects the concentration of nitrogen oxide as detected by the nitrogen oxide concentration detection means depending on an offset from the target temperature of the temperature of the oxygen concentration measurement cell detected by the temperature detection means for temperature-compensating a detected value of the concentration of nitrogen oxides. Therefore, with the present aspect, if the temperature of the main body portion of the sensor cannot be controlled to be equal to the target temperature despite the fact that the heater current supply control is being carried out by the heater current control means, the results of detection of the NOx concentration can be compensated for temperature by the correction means for further improving the detection accuracy of the NOx concentration.

Specifically, should the gas under measurement be changed suddenly in temperature, it may be an occurrence that the temperature of the main body portion of the sensor cannot be sufficiently controlled by temperature control by the heater current supply control means such that the temperature of the main body portion of the sensor is momentarily changed with changes in temperature of the gas under measurement. According to the present invention, the NOx concentration can be detected accurately even in such case thus further improving detection accuracy of the NOx concentration.

Although the temperature detection means for detecting the temperature of the oxygen concentration measurement cell may be implemented by providing a temperature-sensor device in the vicinity of the oxygen concentration measurement cell, the main body portion of the sensor becomes complex in this case. Moreover, it is difficult to measure the oxygen concentration measurement cell itself accurately.

It is therefore desirable to design the temperature sensor mans for detecting the internal resistance of the oxygen concentration measurement cell and to control the current supply to the heater so that the detected internal resistance of the oxygen concentration measurement cell will be of a (e.g., pre-set) value corresponding to the target temperature.

That is, the internal resistance of the oxygen concentration measurement cell is changed with the temperature of the oxygen concentration measurement cell (the internal resistance becomes lower the higher becomes the temperature), so that, if the internal resistance of the oxygen concentration measurement cell is detected as follows according to a third aspect. The temperature of the oxygen concentration measurement cell can be accurately detected from the detected internal resistance, without the necessity of providing a temperature-detection device in the main body portion of the sensor, thus enabling temperature control of the main body portion of the sensor to be carried out more easily and accurately.

If the internal resistance of the oxygen concentration measurement cell is detected in this manner by temperature detection means. The temperature detection means may be such means as either (a) applying a constant voltage for internal resistance detection across the oxygen concentration measurement cell for detecting the intensity of the current flowing at this time in the oxygen concentration measurement cell, (b) or such means as flowing a constant current for internal resistance detection across the oxygen concentration measurement cell thereupon to detect the voltage across both terminals of the oxygen concentration measurement cell.

However, for detecting the internal resistance of the oxygen concentration measurement cell in this manner, it is necessary to momentarily disconnect the pump current control means from the oxygen concentration measurement cell to stop current supply control for the first oxygen pumping cell by the pump current control means. That is, if the current is supplied to the oxygen concentration measurement cell for detecting the internal resistance, the voltage across both ends of the cell becomes non-coincident with the oxygen concentration in the first measurement chamber, such that the control operation of the pump current control means, if continued, leads to erroneous control of the oxygen concentration in the first measurement chamber. Thus, for evading this erroneous control, the control operation by the pump current control means is desirably discontinued for possibly evading this erroneous control.

The oxygen concentration measurement cell is for detecting the oxygen concentration in the first measurement chamber. Among the paired porous electrodes making up the cell, one electrode that is not contacted with the first measurement chamber needs to be of a constant value. To this end, a reference gas of a constant oxygen concentration, such as atmospheric air, can be introduced into this electrode side. However, if this reference gas is introduced in this manner from outside, it is necessary to provide a gap (conduit) in the main body portion of the sensor for introducing the reference gas, thus complicating the structure of the main body portion of the sensor.

According to a fourth aspect, for setting the reference oxygen concentration on the side of the porous electrode opposite to the first measurement chamber of the oxygen concentration measurement cell, it suffices if the porous electrode of the oxygen concentration measurement cell on the opposite side with respect to the first measurement chamber in the main body portion of the sensor is closed, such that a portion of oxygen in the closed space can leak to outside via a leakage resistance. The pump current controlling means causes the small current to flow in the oxygen concentration measurement cell in a direction of pumping out oxygen in the first measurement chamber into the closed space to control the amount of the current flowing in the first oxygen pumping cell so that the electromotive force generated in the oxygen concentration measurement cell will be of a constant value, while the closed spacing functions as an internal oxygen reference source. By so doing, there is no necessity of providing a gap (conduit) for introducing the reference gas into the main body portion of the sensor thus simplifying the structure of the main body portion of the sensor.

For measuring the internal resistance of the oxygen concentration measurement cell by temperature detection means, it is desirable if, as in the fourth aspect, the temperature controlling means periodically interrupts connection between the pump current controlling means and the oxygen concentration measurement cell and causes a current for the internal resistance detection larger than the small current to flow in the oxygen concentration measurement cell in an opposite direction with respect to the small current for detecting the internal resistance of the oxygen concentration measurement cell based on the voltage produced at this time across the electrodes of the oxygen concentration measurement cell.

That is, although the current for detecting the internal resistance can be caused to flow in the same direction as the small current, the current can be caused to flow in the opposite direction to the usual current flowing direction for suppressing electrode deterioration for manifesting the effect of periodically activating the electrode.

Meanwhile, if the current is caused to flow in the oxygen concentration measurement cell, the voltage generated by the oxygen concentration measurement cell is changed not only by the internal resistance of the oxygen concentration measurement cell, but by the oxygen concentration ratio between the electrodes. However, since the values of the oxygen concentration of both electrode sides of the oxygen concentration measurement cell (that is the ratio of the oxygen concentration in the first measurement chamber to that in the closed spacing) remains substantially constant by supplying the small current and by performing current supply control for the first oxygen pumping cell by the pump current control means, the electromotive force remains substantially constant during the supply period of the current for detecting the internal resistance. Besides, the back electromotive force generated by the current for the internal resistance detection is relatively large as compared with the variation in the electromotive force of the oxygen concentration measurement cell. Thus, according to the present invention, the internal resistance of the oxygen concentration measurement cell can be detected without being affected by changes in the electromotive force.

If the current for detecting the internal resistance is caused to flow in the oxygen concentration measurement cell in this manner through the oxygen concentration measurement cell, since the oxygen concentration measurement cell is changed in its direction of polarization in the solid electrolyte or between the solid electrolyte and the electrode, such that the electromotive force cannot be developed immediately depending on the ratio between the oxygen concentration in the first measurement chamber and that in the closed space in the same way as before measurement, thus giving a slightly offset value of the electromotive force. Therefore, it takes some period of time until this polarization is annulled to enable the oxygen concentration measurement cell to accurately detect the oxygen concentration in the first measurement chamber, such that, even if the control operation of the pump current control means is re-initiated directly following detection of the internal resistance, the NOx concentration cannot be detected accurately.

According to a fifth aspect, the following consideration is added.

For shortening the period of time which elapses after detection of the internal resistance until realization of correct measurement of the NOx concentration (non-detecting time), it suffices if the temperature detection means causing the current for internal resistance detection to flow in the oxygen concentration measurement cell for detecting the internal resistance, the temperature detection means subsequently causing a current larger than the small current to flow in the oxygen concentration measurement cell in an opposite direction to the current for detecting the internal resistance.

That is, if the current for detecting the internal resistance is caused to flow alternately in pulsed fashion through the oxygen concentration measurement cells, the oxygen concentration in each electrode side of the oxygen concentration measurement cell can be quickly reset to the stable state prevailing prior to detection of the internal resistance, thus shortening the period of time which elapses after detection of the internal resistance until realization of correct measurement of the NOx concentration.

According to the present invention, the temperature of one of the three cells of the main body portion of the sensor, i.e., one detecting the oxygen concentration in the first measurement chamber, which one most significantly influences the detecting accuracy of the NOx concentration, is detected as being the temperature of the main body portion of the cell to control the current supplied to the heater. However, it may be an occurrence that, depending on the structure of the main body portion of the cell, the temperature of the first or second oxygen pumping cell cannot be controlled close to the target temperature.

For realizing the effect of temperature control of the present invention more satisfactorily, in the main body portion of the sensor, the first oxygen pumping cell, oxygen concentration measurement cell and the second oxygen pumping cell are formed as respective different sheet-shaped solid electrolytes, whilst the first measurement chamber and the second measurement chamber are formed by laminating the solid electrolyte layers with a gap between neighboring layers so that the solid electrolyte layers formed with the first oxygen pumping cell and the second oxygen pumping cell face outwards. The heater is made up of two sheet-shaped heater substrates with heater wire patterns formed thereon. The heater substrate is arranged with a pre-set gap between the neighboring layers on both sides of the laminating direction of the solid electrolyte layers in the main body portion of the sensor for heating the main body portion of the sensor. Preferably, the first diffusion layer is formed at a portion of the solid electrolyte layer provided with the first oxygen pumping cell, this portion including an area opposing the mid portion of the heater wire patterns of the heater substrates.

That is, if the main body portion of the sensor and the heaters are designed as described above, the solid electrolyte layer, provided with the oxygen concentration measurement cell, is sandwiched between the solid electrolyte layers provided with the first oxygen pumping cell and the second oxygen pumping cell, and heater substrates are arranged on both side in the laminating direction, so that if the temperature of the oxygen concentration measurement cell is controlled to be the target temperature by the current supply control to the heater, the first and oxygen pumping cells can be controlled more reliably to the target temperature. Moreover, the gas under measurement, flowing from the first diffusion layer and the second diffusion layer, can be heated sufficiently by the heater.

The result is that, according to a sixth aspect of the present invention, temperature fluctuations of respective cells of the main body portion of the cell become harder to occur, whilst the cells become difficult to be affected by the temperature of the gas under measurement, thus further improving NOx concentration detection accuracy.

According to a seventh aspect of the present invention, if, in this case, second diffusion rate defining layer is formed for being partially registered (overlapped) with at least a portion of the first diffusing speed determining layer when the main body portion of the sensor is projected from the layering direction of the solid electrolyte layers, and the oxygen concentration measurement cell is arranged in the vicinity of the second diffusion rate defining layer, the temperature of the main body portion of the sensor and the gas under measurement can be controlled more reliably to the target temperature, thus improving the NOx concentration detection accuracy.

EXAMPLES

Figure 1:
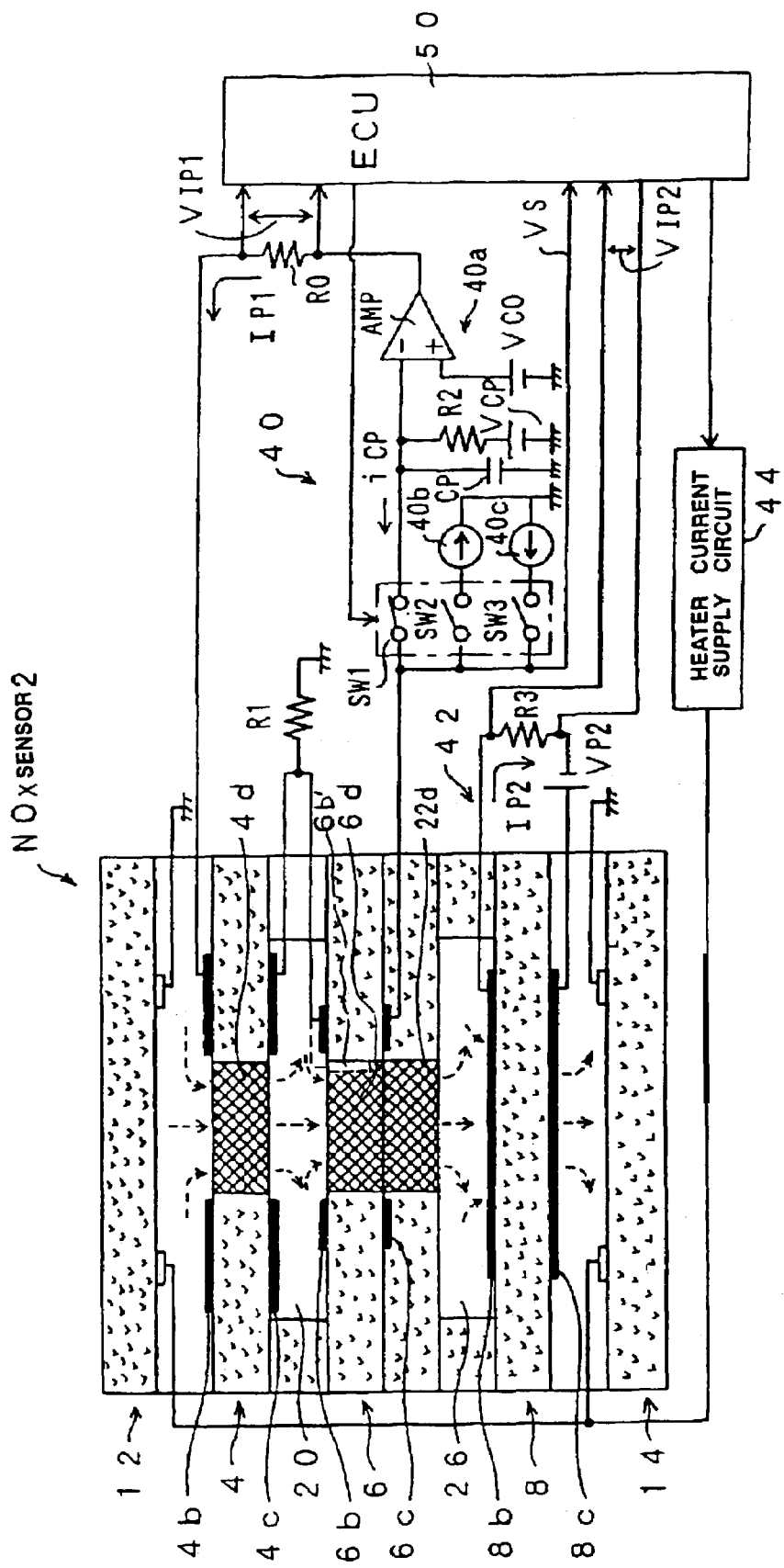
FIG. 1 is a schematic view showing the entire structure of a nitrogen oxide concentration detection device embodying the present invention.

Referring to the drawings, a preferred embodiment of the present invention will be explained in detail.

Figure 2:
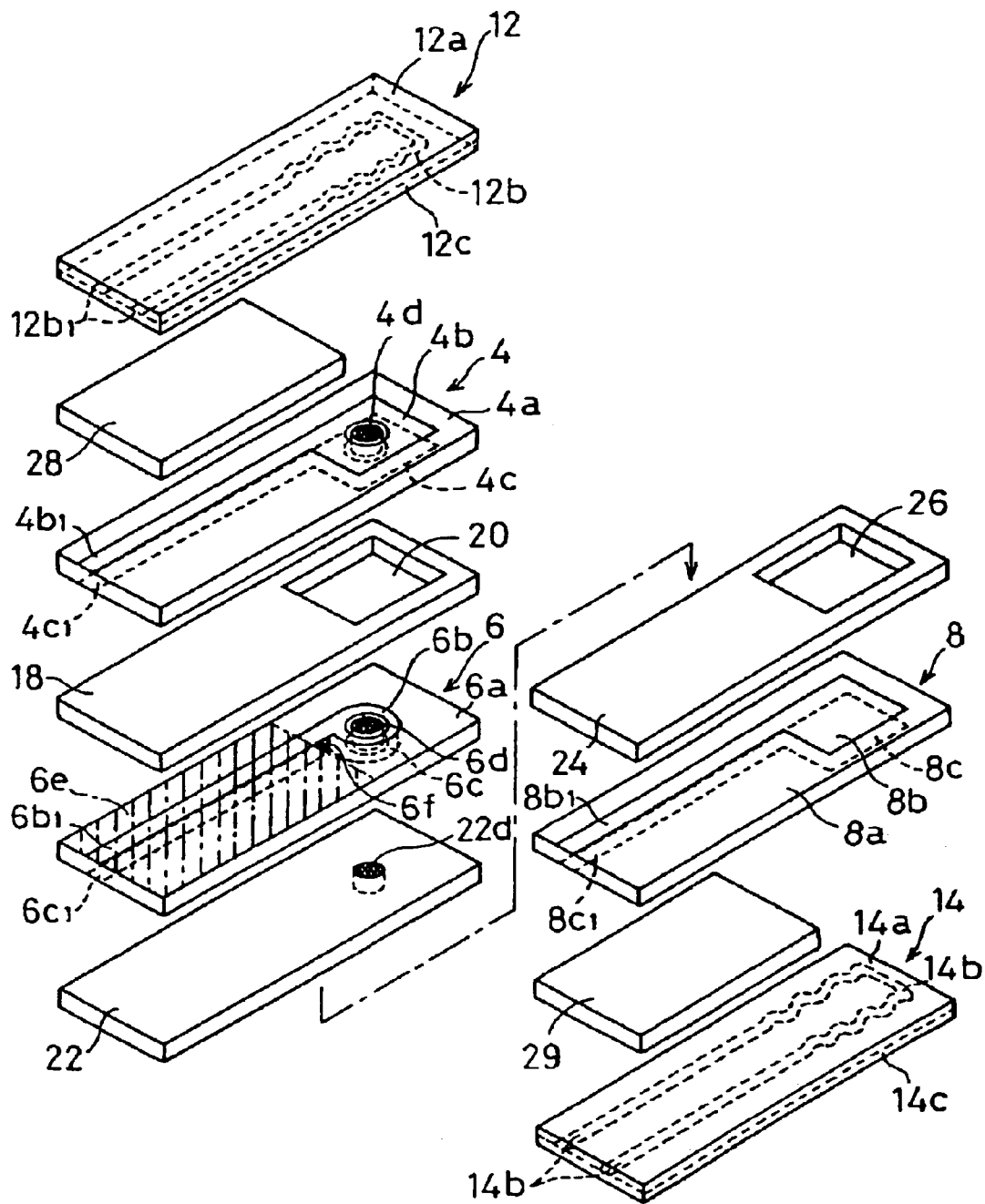
FIG. 2 is an exploded perspective view showing the structure of the NOx sensor of the detection device shown in FIG. 1.

FIG. 1 schematically shows the structure of the overall nitrogen oxide concentration detection device embodying the present invention and FIG. 2 shows, in an exploded perspective view, an NOx sensor 2 employed in the nitrogen oxide concentration detection device.

Referring to FIG. 1, the nitrogen oxide concentration detection device includes a NOx sensor 2 as a main body portion of the sensor, a first oxygen pumping cell (first pump cell) 4 constituting the NOx sensor 2, and a driving circuit 40 for current supply and for switching the current path to an oxygen concentration measurement cell (Vs cell) 6. The nitrogen oxide concentration detection device also includes a detection circuit 42 for applying a constant voltage across second oxygen pumping cell (second pump cell) 8 making up the NOx sensor 2, a heater current supplying circuit 44 for supplying the current across a pair of heaters 12, 14 provided on the NOx sensor 2 for heating cells 4, 6 and 8 and an electronic control circuit (ECU) 50 comprised of a microcomputer for driving-controlling the driving circuit 40 and the heater current supplying circuit 44 and for calculating the NOx concentration in the gas under measurement based on a detection signal VIP2 from the detection circuit 42.

Referring to FIG. 2, the first pump cell 4 in the NOx sensor 2 includes rectangular-shaped porous electrodes 4b, 4c and lead portions 4b1, 4c1 on both sides of a plate-shaped solid electrolyte layer 4a. The NOx sensor 2 also includes a diffusion rate defining layer 4d formed by padding a porous filler into a round hole bored in the plate-shaped solid electrolyte layer 4a traversing the mid portions of the porous electrodes 4b, 4c.

Similarly to the second pump cell 8, the Vs cell 6 includes rectangular-shaped porous electrodes 6b, 6c and lead portions 6b1, 6c1 on both sides of a plate-shaped solid electrolyte layer 6a. The NOx sensor 2 also includes a diffusion rate defining layer 6d formed by padding a porous filler into a round hole bored in the plate-shaped solid electrolyte layer 6a, traversing the mid portions of the porous electrodes 6b, 6c.

The porous electrodes 6b, 6c of the Vs cell 6 and the porous electrodes 4b, 4c of the first pump cell 4 are arranged relative to each other so that the center positions thereof on the solid electrolyte layers 4a, 6a are substantially coincident with each other, such that, when the Vs cell 6 and the first pump cell 4 are laminated together, the diffusion rate defining layers 6a, 4a face each other. The circular (annular) porous electrodes 6b, 6c formed in the Vs cell 6 are smaller than the rectangular-shaped porous electrodes 4b, 4c formed in the Vs cell 6. On the front and back sides of the Vs cell 6 are formed insulating films 6e of, for example, alumina, for covering the lead portions 6b1, 6c1 from outside for preventing current leakage from the lead portions 6b1, 6c1. Between the lead portions 6b1, 6c1 is formed a leakage resistance portion 6f for leaking part of oxygen pumped towards the porous electrode 6c by current control as later explained towards the porous electrode 6b.

The first pump cell 4 and the Vs cell 6, formed as described above, are laminated together via an intervening solid electrolyte layer 18 of the same shape as the solid electrolyte layers 4a, 6a. At a facing portion of the porous electrodes 4c, 6c, a rectangular-shaped opening larger than the porous electrode 4c is bored in the solid electrolyte layer 18, this opening operating as a first measurement chamber 20.

On the porous electrode 6c of the Vs cell 6 is laminated a solid electrolyte layer 22 of the same shape as the solid electrolyte layers 4a, 6a. This solid electrolyte layer 22 has a round hole which is bored at the same position as the diffusion rate defining layer 6d of the Vs cell 6 and into which is charged a porous filler for forming a diffusion rate defining layer 22d.

Similarly to the first pump cell 4, the second pump cell 8 has rectangular-shaped porous electrodes 8b, 8c and lead portions 8b1, 8c1. This second pump cell 8 is laminated on a solid electrolyte layer 22, laminated on. the Vs cell 6, via a solid electrolyte layer 24 formed similarly to the solid electrolyte layer 18. The result is that the rectangular-shaped opening formed in the se layer 24 operates as a second measurement chamber 26.

On both sides of the laminated assembly of the first pump cell 4, Vs cell 6 and the second pump cell 8, that is on an outer sides of the first pump cell 4 and the second pump cell 8, are laminated heaters 12, 14 via spacers 28, 29 for providing a pre-set gap.

The heaters 12, 14 are made up of heater substrates 12a, 12c, 14a, 14c of the same shape as the solid electrolyte layers 4a, 6a, . . . and heater wires 12b, 14b with associated lead portions 12b1, 14b1. The heater wires (patterns) 12b, 14b are sandwiched between the heater substrates 12a, 12c and between the heater substrates 14a, 14c and embedded in the heater substrates. Between the heaters 12, 14 and the first pump cell 4 and the second pump cell 8 are formed spacers 28, 29 so that the heaters 12, 14 face the porous electrode 4b of the first pump cell 4 and and the porous electrode 8c of the second pump cell 8, each via a gap, respectively.

The solid electrolyte making up the solid electrolyte layers 4a, 6a, . . . may be typified by a solid solution of zirconia-yttria and a solid solution of zirconia-calcia. In addition, solid solutions of hafnia. The perovskite type oxide solid solution or a trivalent metal oxide solid solution may also be used. The porous electrodes provided on the surfaces of the solid electrolyte layers 4a, 6a facing the first measurement chamber are made up preferably of a material capable of controlling or suppressing the decomposition of NOx, e.g., Pt or Pt alloy with a suppressive component(s) of the catalitic action of Pt such as Au, Pb, Ag, etc. On the other hand the porous electrodes facing the second measurement chamber are preferably formed of platinum, rhodium or alloys thereof having catalytic functions capable of decomposing NOx. For forming the porous electrodes, there have so far been known a thick-film forming method of screen-printing a paste of a mixture of platinum powders and powders of the same material as the solid electrolyte layer on a solid electrolyte layer and firing the resulting mass, and a method of forming a coating by flame spraying. For the diffusion rate defining layers 4d, 6d and 22d, ceramics having fine through-holes or porous ceramics are preferably employed.

The heater wires 12b, 14b are preferably formed of a composite material of ceramics and platinum or platinum alloys, while lead portions 12b1, 14b1 are preferably formed of platinum or platinum alloys for lowering the resistance value for reducing electrical losses at the lead portions. For the heater substrates 12a, 12b, 14a, 14c and for the spacers 28, 29, alumina, spinel, forsterite, steatite or zirconia etc. may be used.

In particular, it is meritorious for fabricating the NOx sensor 2 if the heater substrates and the spacers are formed of zirconia, because the heaters and the pump cells are unified and fired simultaneously. In this case, insulating layers of, for example, alumina, are provided between the heater substrate 12b and its lead portion 12b1 and the heater substrates 12a, 12c and between the heater substrates 14a, 14c and lead portions 14b1, 14c1 thereof and the heater substrates 14a, 14c.

If alumina is used for the heater substrate, a porous material may be used as a spacer for preventing cracks from being formed due to difference in thermal shrinkage rate or coefficient of thermal expansion during firing for connection to each pump cell. It is also possible to fire the heaters and the pump cells separately and subsequently cement them together using a cement or the like inorganic material as a cementing agent serving simultaneously as a spacer.

Referring to FIG. 1, the porous electrodes 4c, 6b towards the first measurement chamber 20 of the Vs cell 6 and the first pump cell 4 of the NOx sensor 2 are grounded via a resistor R1, whilst the opposite side porous electrodes 4b, 6c are connected to a driving circuit 40.

As an alternative configuration for the porous electrode 6b, disposed facing the first measurement chamber 20, of the Vs cell, a porous electrode 6b', e.g., as shown by a broken line in FIG. 1, may be disposed at a different position (or positions), for instance, at an entrance or exit part of, or within, the second diffusion rate defining layer 6d that is located between the first and second measurement chambers.

The driving circuit 40 has a controller 40a having a resistor R2, to one end of which a constant voltage VCP is applied and the opposite end of which is connected via a switch SW1 to the porous electrode 6c of the Vs cell 6. The driving circuit 40 also has a differential amplifier AMP to an inverted side input terminal (−) of which are connected the porous electrode 6c and the Vs cell 6 via a switch SW1 and one terminal of a capacitor Cp and to a non-inverted side input terminal (+) of which is connected a reference voltage VCO. The differential amplifier has its output terminal connected via resistor R0 to the porous electrode 4b of the first pump cell 4. The opposite terminal of the capacitor Cp is grounded.

When the switch SW1 is on, this controller 40a operates as follows:

First, a constant small current iCP is caused to flow through the Vs cell 6 via resistor R2 for pumping oxygen in the first measurement chamber 20 towards the porous electrode 6c of the Vs cell 6. Since this porous electrode 6c is closed by the solid electrolyte layer 22 and communicates with the side of the porous electrode 6b via the leakage resistance 6f, the closed space within the porous electrode 6c is at a constant oxygen concentration and operates as an internal oxygen reference source.

If the side of the porous electrode 6c of the Vs cell 6 operates as the internal oxygen reference source, an electromotive force proportionate to the ratio of the oxygen concentration in the first measurement chamber 20 and the oxygen concentration towards (on the side of) the internal oxygen reference source is generated in the Vs cell 6, with the voltage Vs towards the porous electrode 6c being of a value proportionate to the oxygen concentration in the first measurement chamber 20. Since this voltage is applied across the differential amplifier AMP, the differential amplifier AMP outputs a voltage proportionate to an offset between the reference voltage VCO and the input voltage (VCO-input voltage). This output voltage is applied via resistor R10 across the porous electrode 4b of the first pump cell 4.

The result is that the current (first pump current) IP1 flows through the first pump cell 4. This first pump current IP1 controls the electromotive force generated in the Vs cell 6 to be a constant voltage. That is, the first pump current IP1 controls the oxygen concentration in the first measurement chamber 20 to be of a constant value.

That is, the controller 40a operates as pump current control means of the present invention and manages controls for pumping oxygen to outside of the first measurement chamber 20 so that the oxygen concentration in the gas under measurement which has flown into the first measurement chamber 20 via diffusion rate defining layer 4d will be of a pre-set value.

The oxygen concentration in the first measurement chamber 20, thus controlled, is set to allow the presence of a small amount of oxygen to be of a low value of the order of, for example, 100 ppm, so as not to have NOx components largely or completely decomposed in the gas under measurement in the first measurement chamber 20 by current conduction of the first pump current IP1. The reference voltage VCO, which determines this oxygen concentration, is set to a value of the order of 100 mV to 200 mV. A resistor R0, connected across an output of the differential amplifier AMP and the porous electrode 4b, is used for detecting the first pump current IP1. A voltage VIP1 across its both terminals is entered as a detection signal of the first pump current IP1 is entered to the ECU 50 as a detection signal of the first pump current IP1.

The driving circuit 40 includes, in addition to the above-mentioned controller 40a, a constant current circuit 40b connected via a switch SW2 to a porous electrode 6c and adapted for flowing the constant current through the porous electrodes 6b, 6c in an opposite direction to the small current iCP, and a constant current circuit 40c connected via a switch SW3 to the porous electrode 6c and adapted for flowing the constant current through the porous electrodes 6c, 6b in the same direction as the small current iCP These constant current circuits 40b, 40c detect the internal resistance RVS of the Vs cell 6. In order for the internal resistance RVS of the Vs cell 6 to be detected on the side of the ECU 50 by the supply of this constant current, the voltage Vs on the side of the porous electrode 6c is entered to the ECU 50. The constant currents flowing in the constant current circuits 40b, 40c are set so as to be equal in magnitude and opposite in the flowing directions. The current value is larger than the minor current iCP supplied via resistor R2 to the Vs cell 6.

The switches SW1 to SW3, provided between the controller 40a, constant current circuits 40b, 40c and the Vs cell 6 are turned on and off by the control signal from the ECU 50. During the normal operation when detecting the NOx concentration, only the switch SW1 is turned on to activate the controller 40a. The switch SW1 is turned off only during the detection of the internal resistance RVS of the Vs cell 6, with the switches SW2 and SW3 being controlled to be turned on sequentially.

There is applied, across the porous electrodes 8b, 8c of the second pump cell 8 of the NOx sensor 2, a constant voltage VP2 via a resistor R3 as constant voltage applying means making up the detection circuit 42. The direction of applying the constant voltage VP2 is set so that the porous electrodes 8c, 8b will be of positive and negative polarities, respectively, so that the current will flow from the porous electrode 8c to the porous electrode 8b to pump oxygen from the second measurement chamber 26 to outside. Also, the constant voltage VP2 is set to a value (e.g., 450 mV) such as to decompose NOx components in the measurement gas in the second measurement chamber flowing from the first measurement chamber 20 via diffusion rate defining layers 6d, 22d to pump out the oxygen component.

The resistor R3 is used for converting the second pump current IP2 flowing in the second pump cell 8 on application of the constant voltage VP2 into a voltage VIP2 for entering the converted voltage VIP2 as a detection signal of the second pump current IP2 to the ECU 50.

In the above-described embodiment of the nitrogen oxide concentration detection device, if the switch SW1 in the driving circuit 40 is turned on and the switches SW2, SW3 are turned off, the oxygen concentration in the first measurement chamber 20, into which flows the measurement gas via diffusion rate defining layer (first diffusion rate defining layer 4d), is controlled to a constant oxygen concentration. The measurement gas, thus controlled to the constant oxygen concentration, flows into the second measurement chamber 26 via diffusion rate defining layers 6d, 22d, so that the second pump current IP2, flowing in the second pump cell 8, is hardly influenced by the oxygen concentration in the measurement gas and is varied with the NOx concentration. Thus, by reading the detection signal VIP2 of the second pump current IP2 on the side of the ECU 50, and by executing pre-set calculating operations, the NOx concentration in the measurement gas can be detected from the detection signal VIP2, that is from the second pump current IP2.

It should be noted that, for realizing detection accuracy of the NOx concentration, the temperature of the cells 4, 6, 8, in particular the temperature of the Vs cell 6 adapted for detecting the oxygen concentration in the first measurement chamber 20, needs to be controlled to a constant value. To this end, the current supplied from the heater current supplying circuit 44 to the heaters 12, 14 needs to be controlled to a target temperature. In the present embodiment, the ECU 50 switches the on/off state of the switches SW1 to SW3 to detect the temperature of the Vs cell 6 from its internal resistance RVS and the current supply from the heater current supplying circuit 44 to the heaters 12, 14 is controlled so that the detected internal resistance RVS will be of a pre-set (e.g., constant) value, that is so that the temperature of the Vs cell 6 will be a target temperature.

Figure 3:
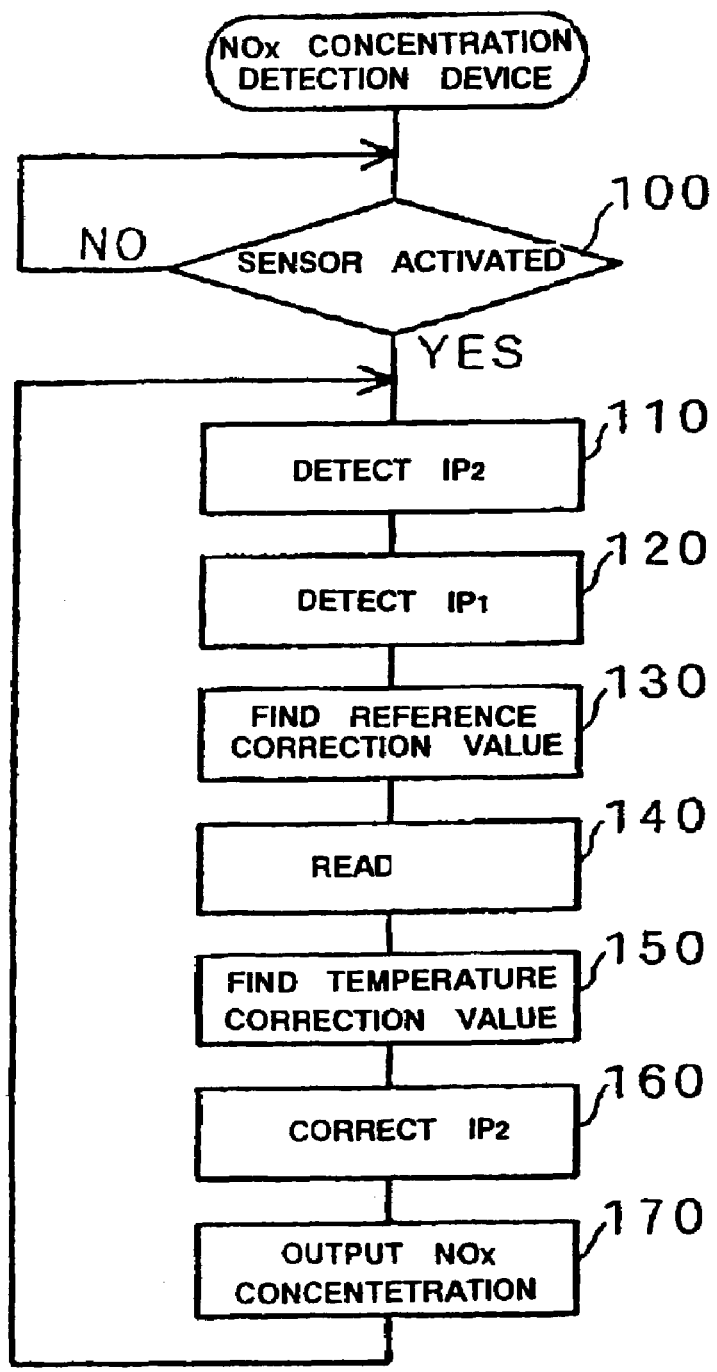
FIG. 3 is a flowchart showing the processing for detecting the NOx concentration repeatedly executed by an ECU of the detection device shown in FIG. 1.
Figure 4:
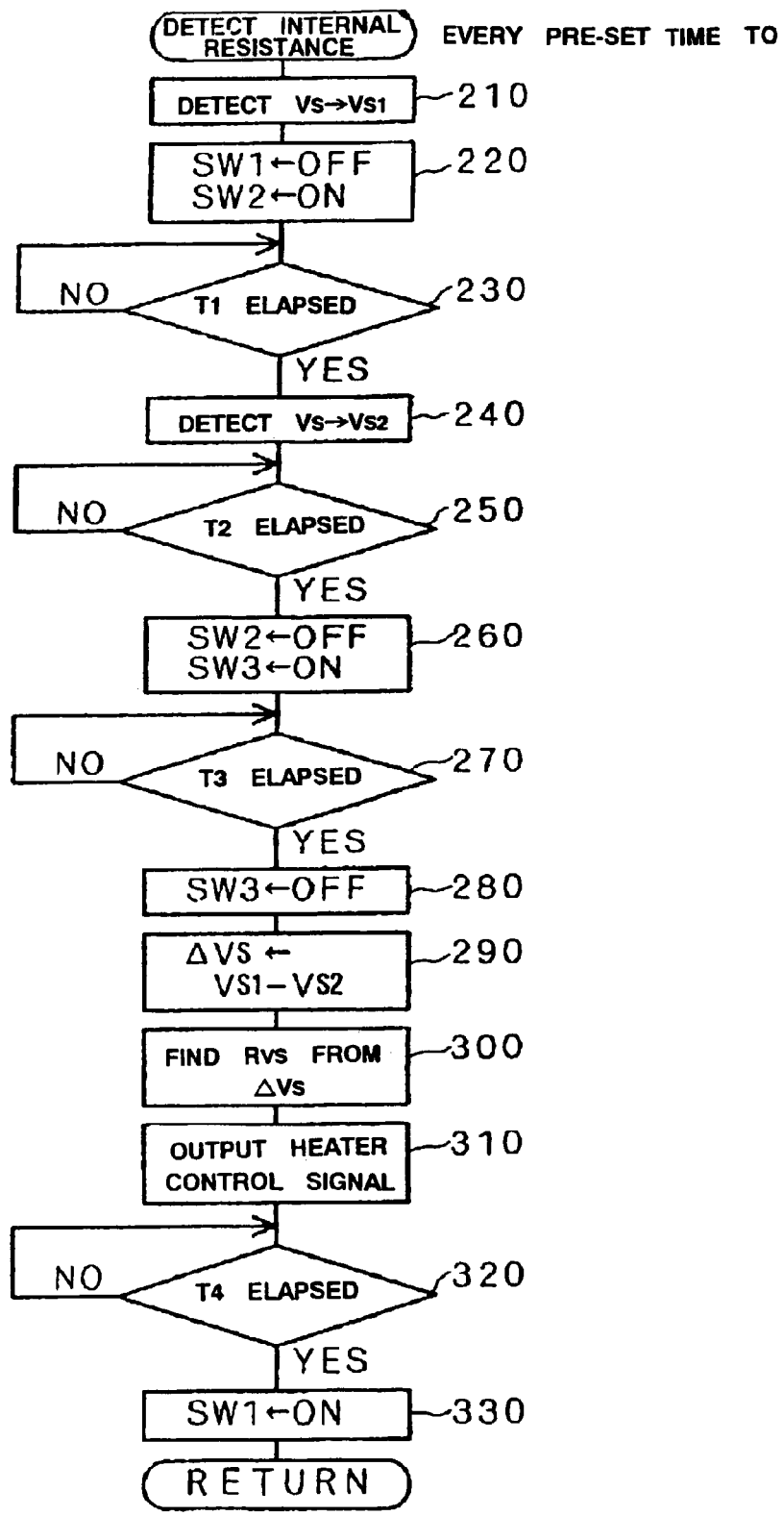
FIG. 4 is a flowchart showing the processing for detecting the internal resistance executed as an interrupt processing every pre-set time interval by the ECU of the detection device shown in FIG. 1.

Referring to the flowcharts shown in FIGS. 3 and 4, the control processing executed by the ECU 50 for performing the above temperature control and for detecting the NOx concentration is explained in detail.

FIG. 3 shows the NOx concentration detection processing repeatedly carried out by the ECU 50 for detecting the NOx concentration, while FIG. 4 shows the processing for detecting the internal resistance executed as an interrupt operation every pre-set time TO (such as every second) by the ECU 50 for controlling the current supply to the heaters 12, 14.

Referring to FIG. 3, at step S100 of the processing for NOx concentration detection, it is judged after starting the detection device whether or not the NOx sensor 2 has been activated by current supply to the heaters 12, 14 for waiting for activation of the NOx sensor 2, by way of processing for activation discrimination.

Figure 5:
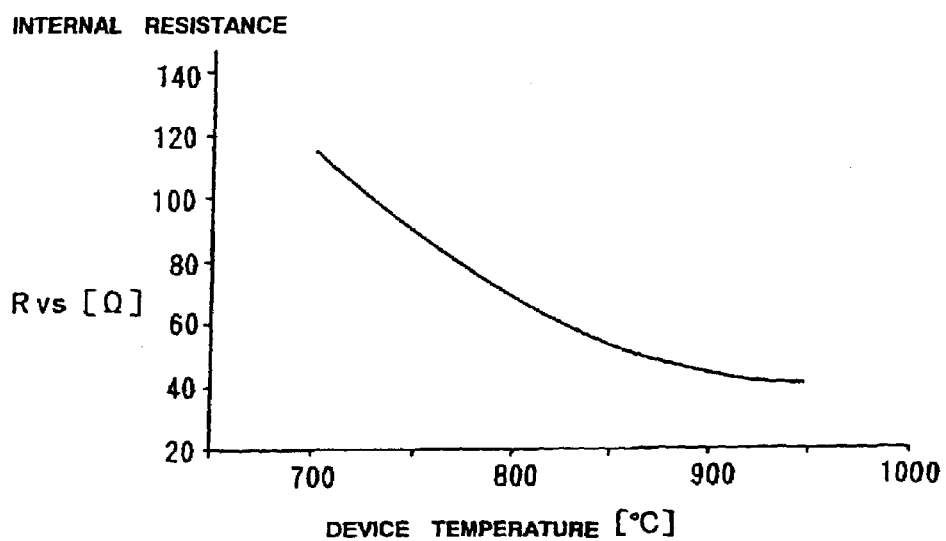
FIG. 5 is a graph showing the relation between the internal resistance of the oxygen concentration measurement cell and the device temperature.

This activation discrimination is carried out by judging whether or not the internal resistance RVS of the Vs cell as detected by processing for internal resistance detection (which will be explained later) has become lower than a pre-set activation discrimination value. Specifically as shown in FIG. 5, since the internal resistance RVS of the Vs cell 6 is decreased with an increasing device temperature and activation of the Vs cell 6, it is judged at step S100 whether or not, after start of current supply to the heaters 12, 14, the internal resistance RVS of the Vs cell has become lower than the activation discrimination value for judging whether or not the device temperature has reached a pre-set activation temperature.

It should be noted that, directly after starting of the detection device, the switch SW1 and the switches SW2, SW3 in the driving circuit 40 are controlled to be turned on and off, respectively, by initializing processing, not shown, and that, during the time the temperature of the NOx sensor 2 is raised to near the activation temperature by the activation processing at step S100, the differential amplifier AMP in the driving circuit 40 is not operated.

If at step S100 the NOx sensor 2 is judged to have been activated, processing transfers to step S110 to read the detection signal VIP2 entered from the resistor R3 of the detection circuit 42 to detect the second pump current IP2. At the next step S120, the detection signal VIP1 entered from the resistor R0 of the driving circuit 40 is read to detect the first pump current IP1. At the next step S130, a reference correction value for the second pump current IP2 is calculated based on the detected first pump current IP1.

Figure 6:
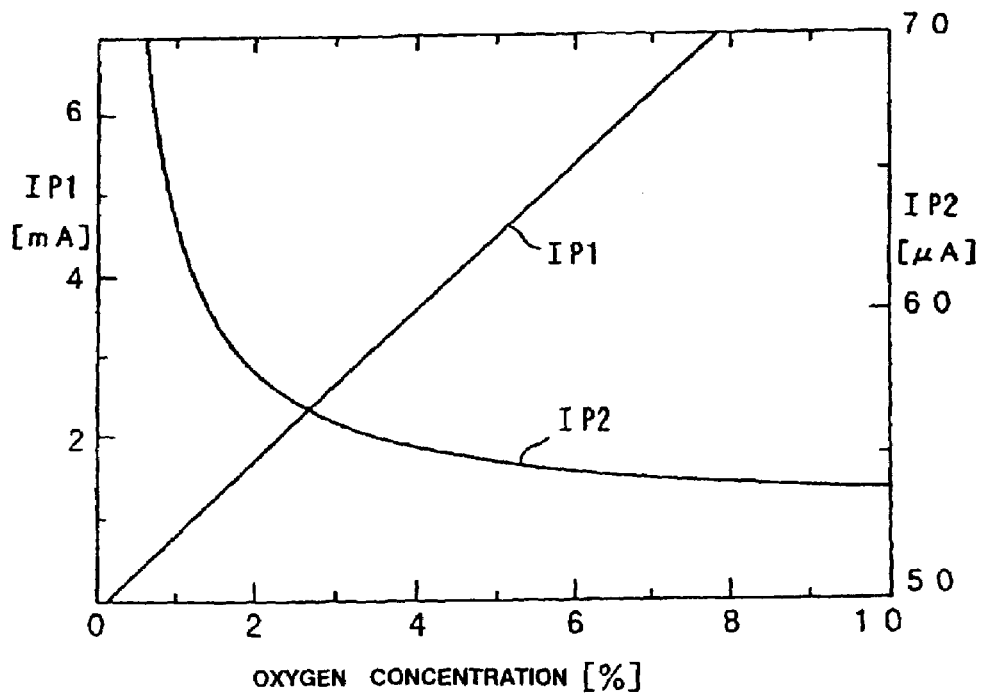
FIG. 6 is a graph showing the relation between the oxygen concentration of the NOx-free measurement gas and the first and second pump currents.

That is, in the present embodiment, the oxygen concentration in the first measurement chamber 20 is controlled to be low, so as not to have the NOx components in the gas under measurement largely or completely decomposed in the first measurement chamber 20, by pump current control by the driving circuit 40. It should be noted that not only NOx in the gas under measurement but also oxygen left in the first measurement chamber flows into the second measurement chamber 26. Thus, the second pump current IP2, which is changed in association with the NOx concentration in the gas under measurement, also is affected, if only slightly, by the oxygen concentration in the measurement gas. FIG. 6 shows an illustrative result of measurement of the first pump current IP1 and the second pump current IP2, when the device is run in operation, using a NOx-free test gas as a gas under measurement. As may be seen form this figure, the first pump current IP1 is varied with a constant gradient versus the oxygen concentration in the measurement gas, whilst also the second pump current IP2 is varied under the influence of the oxygen concentration in the measurement gas. This influence (i.e., gradient) on the IP2 becomes stronger the lower the oxygen concentration.

In order for the second pump current IP2 to correspond only to the NOx concentration in the measurement gas, the value of the second pump current IP2 versus the oxygen concentration obtained on measuring the NOx-free gas under measurement is previously stored in a storage medium, such as RCM, as an offset value for correcting the second pump current IP2, the oxygen concentration in the measurement gas is detected from the first pump current IP1 and the offset value corresponding to this oxygen concentration is read out from the pre-stored offset value data for setting as the above-mentioned reference correction value.

For practically calculating this reference correction value, a map storing on memory an offset value associated with the first pump current IP1 (i.e., reference correction value) is used, and is retrieved using the first pump current IP1 as a parameter for directly finding the reference correction value from the first pump current IP1.

If the reference correction value is calculated in this manner, processing transfers to step S140 to read the internal resistance RVS of the Vs cell 6 obtained by the internal resistance detection as later explained. At the next step S150, the temperature correction value for the second pump current IP2 is calculated on the basis of the thus read internal resistance RVS.

That is, in the present embodiment, the internal resistance RVS of the Vs cell 6 is detected in the processing for detecting the internal resistance as later explained and the current supplied to the heaters 12, 14 is controlled so that the internal resistance RVS will be of a pre-set value, that is so that the temperature of the NOx sensor 2 will be a pre-set target temperature. If the temperature of the gas under measurement is varied suddenly, it may be an occurrence that the temperature cannot follow up with temperature variations of the gas under measurement, such that the temperature of the NOx sensor 2 is varied with changes in temperature of the gas under measurement.

Figure 7:
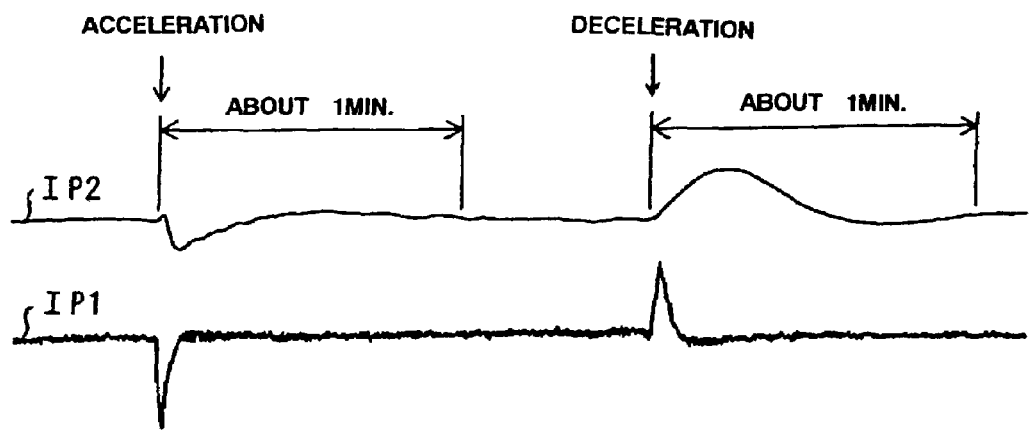
FIG. 7 is a time chart showing changes in the first and second pump currents caused by changes in the exhaust gas temperature during acceleration and deceleration of the internal combustion engine.

FIG. 7 shows an illustrative result of measurement obtained on measuring the temperature changes in the NOx sensor 2 when the NOx sensor 2 is mounted on an exhaust pipe of an internal combustion engine, using a detection device of the present embodiment, and the detection device is actuated. As may be seen from this figure, if, in the detection device of the present embodiment, the NOx sensor temperature is momentarily lowered with an increased amount of air suction during acceleration of the internal combustion engine, or if the NOx sensor temperature is momentarily raised with a decreased amount of air suction during deceleration of the internal combustion engine, despite the fact that the temperature control as later explained is performed, both the first pump current IP1 and the second pump current IP2 undergo variations. In particular, the second pump current IP2 takes about one minute until the stable state is recovered. The reason is that, if the oxygen concentration in the first measurement chamber 20 is offset from the target temperature, it takes much time until the oxygen concentration is restored to the target concentration.

Figure 8:
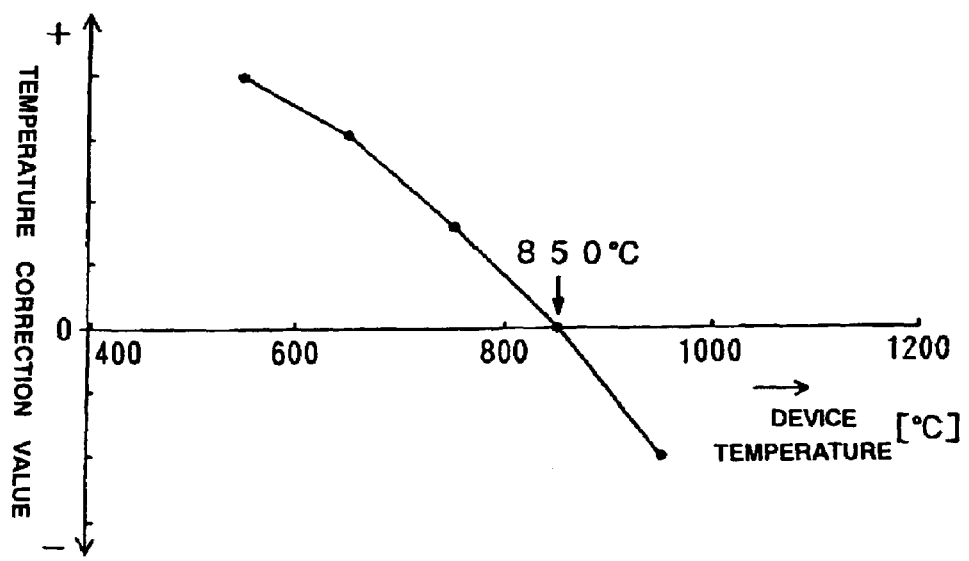
FIG. 8 is a graph showing a map used in finding the temperature correction of the second pump current.

Thus, in the present embodiment, for enabling accurate detection of the NOx concentration from the second pump current IP2 despite sudden changes in the temperature of the gas under measurement, the temperature of the Vs cell 6 is found from the internal resistance RVS of the Vs cell 6 and the amount of temperature compensation for the second pump current IP2 is found using, for example, the map for calculating the temperature correction value, as shown in FIG. 8.

Although the map shown in FIG. 8 is designed for finding the temperature correction value from the device temperature of the Vs cell 6, the temperature correction value can be directly found from the internal resistance RVS, without converting the internal resistance RVS into the temperature, if a map for calculation of the temperature correction value is previously set with the internal resistance RVS of the Vs cell 6 as parameter. It is also possible to pre-set a map having an offset between the device temperature and the target temperature (which is 850° C. in FIG. 8) to find the temperature correction value of the device temperature from the target temperature. Alternatively, it is possible to pre-set a map having an offset (deviation) between the internal resistance RVS and the target resistance value corresponding to the target resistance to find the temperature correction value from the offset (deviation) of the internal resistance RVS from the target resistance value.

If next the temperature correction value is calculated at step S150, processing transfers to step S160 to sum the reference correction value and the temperature correction value to the second pump current IP2 detected at step S110 for correcting the second pump current IP2. At the next step S170, the as-corrected second pump current IP2 is outputted as the NOx concentration, before processing transfers to step S110.

In the present embodiment, the processing of S150 and S160 for correcting the second pump current IP2 depending on the temperature of the NOx sensor 2, more specifically, the Vs cell 6, corresponds to the correction means of the present invention.

In the present embodiment, the reference correction value for correcting the second pump current IP2 based on the first pump current IP1 depending on the oxygen concentration in the measurement gas and the reference correction value for correcting the second pump current IP2 depending on the temperature of the Vs cell 6 are separately found for correcting the second pump current IP2. It is however possible to set a map used for calculating the reference correction value from one temperature of the Vs cell 6 to another and to switch the map used for calculating the reference correction value responsive to the temperature of the Vs cell 6 to find the correction amount for correcting the second pump current IP2 responsive to the oxygen concentration in the measurement gas and to the temperature of the Vs cell 6. Alternatively, it is possible to pre-set a map used for calculating the reference correction value using the first pump current IP1 and the temperature of the Vs cell 6 (or the internal resistance RVS) as parameters and to find the correction value for the second pump current IP2 using this map.

The processing for detecting the internal resistance shown in FIG. 4 is explained. Meanwhile, this processing of detecting the internal resistance has not only the function as temperature detecting means for detecting the internal resistance RVS of the Vs cell 6 but also the function as heater current supply control means for controlling the amount of the current supplied to the heaters 12, 14 via heater current supplying circuit 44 based on the result of detection.

As shown in FIG. 4, when this processing is started, the voltage Vs on the porous electrode 6c of the Vs cell 6 is read at step S210. This voltage Vs is set as a basic detection voltage VS1 of the Vs cell 6. At the next step S220, the switch SW1, so far turned on for detecting the NOx concentration, is turned off, whilst the switch SW2 connected to the constant current circuit 40b is turned on to cause the constant current to flow in the Vs cell 6 in an opposite direction to the small current iCP, that is in a direction of pumping oxygen into the first measurement chamber 20 from the closed space operating so far as an internal oxygen reference source.

At the next step S230, it is checked whether or not a preset time T1, such as 60 μsec, has elapsed after start of the detecting operation, in order to wait for lapse of the pre-set time T1. After lapse of the pre-set time T1, the voltage Vs on the side of the porous electrode 6c of the Vs cell 6 is read and set as being a resistance detection voltage VS2 of the Vs cell 6.

After setting the resistance detection voltage VS2, processing transfers to step S250 to judge whether or not a pre-set time T2, such as 100 μsec, has elapsed after start of the detecting operation, in order to wait for lapse of the pre-set time T2. After lapse of the pre-set time T2, the switch SW2, kept in the on-state for the pre-set time T2 since the start of the processing for detection, is turned off, whilst the switch SW3 connected to the constant current circuit 40c is turned on as shown in step S260, in order to cause the constant current to flow in the Vs cell 6 in the same direction as the small current iCP, that is in the direction of pumping oxygen in the first measurement chamber 20 towards the close space.

With the switch SW3 being turned on in this manner, processing transfers to step S270 to judge whether or not a pre-set time T3, such as 200 μsec, has elapsed after the start of the processing for detection. After lapse of the pre-set time T3, the switch SW3 is turned off at step S280, as a result of which the switches SW1 to SW3 in the driving circuit 40 are all turned off.

At the next step S290, an offset ΔVs between the basic detection voltage VS1 as set immediately after start of the processing for detection and the resistance detection voltage VS2 as set after lapse of the pre-set time T1 (=VS1−VS2) is found. At step S300, the internal resistance RVS of the Vs cell 6 is calculated from the offset ΔVs before processing transfers to step S310. The manner of calculating the internal resistance RVS in the present embodiment will be explained in detail later.

At step S310, a control signal for increasing or decreasing the amount of the supplied current to the heaters 12, 14 based on the offset between the temperature of the Vs cell 6 obtained from the internal resistance RVS of the Vs cell 6 and the target value or the offset from the target temperature of the temperature in the Vs cell 6 obtained from the internal resistance RVS is outputted for controlling the amount of the current supplied to the heaters 12, 14 from the heater current supplying circuit 44 by way of executing the processing as heater current supply control means.

If, in the heater current supply control, the heater current supplying circuit 44 is designed as a switching circuit capable of switching between current supply and non-current-supply at a fast speed, it suffices to control the duty ratio of the driving pulse used for this switching between current supply and non-current-supply. On the other hand, if heater current supplying circuit 44 is designed as a voltage control circuit capable of controlling the output voltage to the heaters 12, 14, it suffices to output the target voltage as the target value of the heater current.

If this heater control signal is outputted, processing transfers to step S320 to judge whether or not a pre-set time T4, such as 500 μsec, has elapsed after start of the detecting operation, in order to wait for lapse of the pre-set time T4. After lapse of the pre-set time T4, the switch SW1, kept in the off-state for the pre-set time T4 after the start of the processing for detection, is turned on as shown in step S320, whilst the switch SW3 connected to the constant current circuit 40c is turned off, in order to terminate the processing for detection to re-initiate the operation of detecting the NOx concentration.

Figure 9:
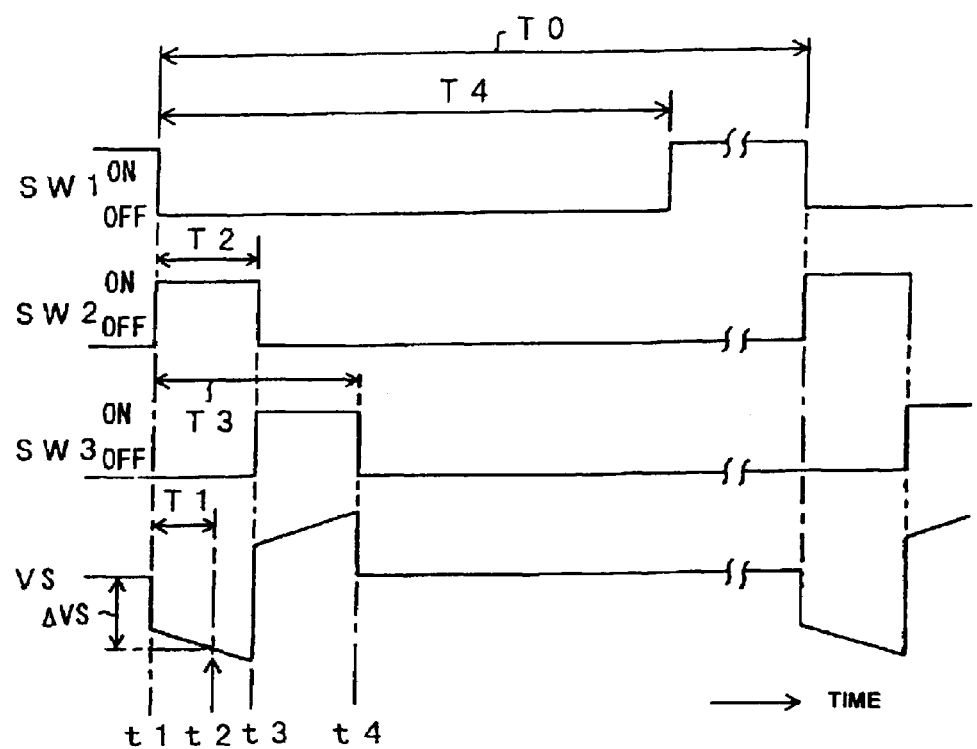
FIG. 9 is a time chart for illustrating the operation of the processing for detecting the internal resistance shown in FIG. 4.

If, in the above-described processing for detecting the internal resistance, the processing is started at time t1 as shown in FIG. 9, the switch SW1 in the driving circuit 40 is turned off to stop the supply of the small current iCP to the Vs cell 6 and the pump current control. At this time, the switch SW2 is turned on to cause the constant current to flow in the Vs cell 6 in an opposite direction to the small current iCP2. After lapse of the pre-set time T1 at time t2, the voltage Vs on the side of the porous electrode 6c at this time is set as a resistance detection voltage VS2. The internal resistance RVS of the Vs cell 6 is detected as an offset ΔVs between the resistance detection voltage VS2 and the voltage Vs on the porous electrode 6c at the time of starting the processing for detection (basic detection voltage VS1). The reason therefor is hereinafter explained.

If the constant current for detecting the internal resistance is caused to flow in the Vs cell 6, the voltage Vs of the porous electrode 6c of the Vs cell 6 is changed not only with the internal resistance RVS of the Vs cell 6 but also with the electromotive force generated responsive to the oxygen concentration on the electrode 6b and that on the electrode 6c. In the present embodiment, the current larger than the small current iCP is caused to flow to increase the voltage drop by the internal resistance RVS of the Vs cell 6 in order for the voltage Vs on the side of the porous electrode 6c for detecting the internal resistance to be less susceptible to the influence of the electromotive force.

Since the oxygen concentration values on the electrodes 6b, 6c of the Vs cell 6 are substantially constant by pump current control and by supply of the small current iCP, the electromotive force of the Vs cell 6 is also substantially constant. Thus, if the constant current is caused to flow in the Vs cell 6 for detecting the voltage Vs of the side of the porous electrode 6c, the internal resistance RVS of the Vs cell 6 can be found from this voltage value substantially accurately.

However, more strictly, the oxygen concentration in the first measurement chamber 20 is controlled by pump current feedback control, so that it is varied by response delay in the control system without being fixed at a constant concentration. Moreover, the oxygen concentration in the first measurement chamber 20 is also varied with the temperature of the NOx sensor 2. Therefore, if the internal resistance RVS is found based on the voltage Vs detected by causing the constant current for detecting the internal resistance RVS to flow in the Vs cell 6, there is produced an error, even if very small, in the internal resistance RVS value.

Thus, in the present embodiment, for more accurate detection of the internal resistance RVS of the Vs cell 6 and hence the device temperature, the variation in the voltage Vs (offset ΔVs) on the side of the porous electrode 6c until a pre-set time, such as 60 μsec, after the supply of the constant current for detecting the internal resistance RVS, is detected, and the internal resistance RVS is found from the offset ΔVs, such that, even if the oxygen concentration in the first measurement chamber 20 is offset from the target concentration, the internal resistance RVS of the Vs cell 6 and hence the device temperature can be found accurately.

In calculating the internal resistance RVS, it suffices if a map storing on memory the internal resistance RVS corresponding to the offset ΔVs is pre-set and the internal resistance RVS is calculated using this map.

In the processing for detecting the internal resistance of the present embodiment, if the pre-set time T1 elapses after start of the processing and the resistance detection voltage VS2 is set at time t2, the switches SW2 and SW3 of the driving circuit 40 are turned off and on, respectively, when the pre-set time, such as 40 μsec, has elapsed, such that the elapsed time after the start of the processing reaches T2 at time t3, in order to cause the constant current to flow in the Vs cell 6 in the same direction as the minor current iCP. If further a pre-set time, such as 100 μsec, has elapsed, such that the elapsed time as from the start of the processing reaches T3 at time t4, the switch SW3 is turned off.

The result is that, in the present embodiment, it becomes possible to relax (dissipate) the polarization in the solid electrolyte of the Vs cell 6 or that between the electrode and the solid electrolyte for detecting the internal resistance RVS, such that the Vs cell 6 can quickly operate as an oxygen concentration cell. Thus, the time T4 which elapses after start of the processing until start of the operation of detecting the NOx concentration can be reduced to, for example, 500 μsec, thus enabling the internal resistance RVS of the Vs cell 6 to be detected to high accuracy without giving influence on the detection operation of the NOx concentration.

In the above-described embodiment of the nitrogen oxide concentration detection device, the temperature of the NOx sensor 2 is detected from the internal resistance RVS of the Vs cell 6, which detects the oxygen concentration in the first measurement chamber 20 most significantly affecting the detection accuracy of the NOx concentration, the current supplied to the heaters 12, 14 is controlled so that the sensor temperature will be equal to the target temperature, such as 850° C. and, if the detected internal resistance RVS or the device temperature obtained therefrom is offset from the target value, the second pump current IP2 representing the results of detection of the NOx concentration is corrected by a temperature correction value corresponding to the offset for temperature-compensating the results of detection of the NOx concentration. Thus, with the present embodiment of the nitrogen oxide concentration detection device, the NOx concentration can be detected at all times to high accuracy without being affected by the temperature of the NOx sensor 2.

In particular, in the present embodiment, the NOx sensor 2 is made up of the first pump cell 4, Vs cell 6 and the second pump cell 8, laminated together in this order, and the heaters 12, 14 laminated on both sides of the layering direction. Also, the heater wires (patterns) 12b, 14b of the heaters 12, 14 are arranged for sandwiching the diffusion rate defining layer 4d and the diffusion rate defining layers 6d, 22a at a mid position so that the diffusion rate defining layer 4d and the diffusion rate defining layers 6d, 22a are superposed together when the NOx sensor 2 is projected from the laminating direction. Therefore, in the present embodiment, the cells 4 to 8 can be efficiently heated using the heaters 12, 14, by virtue of the above-described structure of the NOx sensor 2, while the measurement gas flowing via these diffusion rate defining layers into the first measurement chamber 20 and the second measurement chamber 26 can be heated efficiently. Thus, with the present embodiment, the temperature of each cell of the NOx sensor 2 can be controlled more reliably to the target temperature by controlling the temperature of the Vs cell 6, thus improving the detection accuracy of the NOx concentration.

It should be noted that modifications apparent in the art may be done without departing from the gist and concept disclosed herein within the scope of the claims as appended herewith.

What is claimed is:

1. A nitrogen oxide concentration detection apparatus, comprising:

a main body portion of a sensor having a first measurement chamber, a second measurement chamber, said first measurement chamber formed between a first oxygen pumping cell and an oxygen concentration measurement cell laminated with the first oxygen pumping cell, said first oxygen pumping cell being made of a first oxygen ion conducting solid electrolyte layer formed between porous electrodes, said oxygen concentration measurement cell comprising a second oxygen ion conducting solid electrolyte layer formed between porous electrodes, said first measurement chamber communicating via a first diffusion rate defining layer with a gas under measurement, said second measurement chamber formed between the oxygen concentration cell and a second oxygen pumping cell made of a third oxygen ion conducting solid electrolyte layer formed between porous electrodes, said second measurement chamber communicating with said first measurement chamber via a second diffusion rate defining layer filling a hole penetrating the second oxygen ion conducting solid electrolyte layer constituting said oxygen concentration measurement cell, said oxygen concentration measurement cell being formed as a lamination with the first and second oxygen pumping cells and disposed between said first and second measurement chambers and between said first and third oxygen ion conducting solid electrolyte layers;

a pump current controller for pumping out oxygen from said first measurement chamber by said first oxygen pumping cell so that an output voltage of said oxygen concentration measurement cell will be constant, to control the oxygen concentration in said first measurement chamber to a constant value;

a constant voltage applying unit for applying a constant voltage to said second oxygen pumping cell so as to decompose NOx components of an oxygen-pumped out gas flowed from the first measurement chamber and to pump out oxygen decomposed from the NOx components from the second measurement chamber through said third oxygen ion conducting solid electrolyte layer constituting said second oxygen pumping cell;

a nitrogen oxide concentration detector for detecting a concentration of nitrogen oxides in the gas under measurement based on the current value flowing in said second oxygen pumping cell on application of said constant voltage;

a heater for heating said main body portion of the sensor to a temperature capable of detecting the nitrogen oxide concentration, said heater being formed as a lamination and configured to heat the second oxygen pumping cell and the second measurement chamber and then to heat the first measurement chamber, wherein the first oxygen pumping cell, the oxygen concentration measurement cell and the second oxygen pumping cell are positioned transverse to the lamination and wherein the second oxygen ion conducting solid electrolyte layer constituting the oxygen concentration measurement cell is located between the first and second measurement chambers;

a temperature detector for detecting a temperature of the oxygen concentration measurement cell by detecting an internal resistance of said oxygen concentration measurement cell, the temperature detector being configured to stop current supply control for the first oxygen pumping cell during temperature detecting; and a heater current controller for controlling a current supply to said heater so that the temperature of the oxygen concentration measurement cell detected by said temperature detector will be a pre-set target temperature so that the detected internal resistance of said oxygen concentration measurement cell will be of a value corresponding to said target temperature.

2. The nitrogen oxide concentration detection apparatus of claim 1, wherein, in said main body portion of the sensor, a porous electrode of the oxygen concentration measurement cell on the opposite side with respect to the first measurement chamber is closed, provided that a portion of oxygen in the closed space can leak to outside via a leakage resistance;

wherein said pump current controller causes a small current to flow in said oxygen concentration measurement cell in a direction of pumping out oxygen in said first measurement chamber into said closed space to control the amount of the current flowing in the first oxygen pumping cell so that the electromotive force generated in the oxygen concentration measurement cell will be of a constant value, with the closed space functioning as an integral oxygen reference source; and wherein said temperature detector periodically interrupts connection between said pump current controller and said oxygen concentration measurement cell, and during the interruption a current for internal resistance detection larger than said small current is allowed to flow in said oxygen concentration measurement cell in an opposite direction with respect to the small current to detect the internal resistance of said oxygen concentration measurement cell based on a voltage produced at this time across the electrodes of the oxygen concentration measurement cell.

3. An apparatus for detecting NOx concentration, comprising:

a first measurement chamber formed between a first oxygen pumping cell and an oxygen concentration cell, the first oxygen pumping cell being made of a first oxygen ion conducting solid electrolyte layer, the oxygen concentration measurement cell being made of a second oxygen ion conducting solid electrolyte layer;

a first diffusion rate defining layer formed on the first oxygen ion conducting layer, a gas under measurement flowing through the first diffusion rate defining layer into the first measurement chamber;

a pump current controller for pumping out oxygen of the gas under measurement from said first measurement chamber through said first oxygen pumping cell so that an output voltage of the oxygen concentration measurement cell will be constant;

a second oxygen pumping cell for decomposing nitrogen oxide of the gas under measurement, the second oxygen pumping cell being made of a third oxygen ion conducting solid electrolyte layer and laminated over the oxygen concentration cell;

a second measurement chamber formed between the oxygen concentration measurement cell and the second oxygen pumping cell for decomposing NOx components of the gas under a hole penetrating the second oxygen ion conducting solid electrolyte layer constituting the oxygen concentration measurement cell, the hole being filled with a second diffusion rate defining layer through which the oxygen-pumped out gas flows from the first measurement chamber into the second measurement chamber;

a constant voltage applying unit for applying a constant voltage to the second oxygen pumping cell so as to decompose NOx components flowing from the first measurement chamber and pump out oxygen components decomposed from the NOx components thereby to flow a current across the electrode of the second oxygen pumping cell;

a NOx concentration detector for detecting a concentration of NOx in the gas under measurement based on a value of the current flowing in the second oxygen pumping cell;

a heater for heating the second measurement chamber and then to heat the first measurement chamber to a temperature capable of detecting the NOx concentration;

a temperature detector for detecting a temperature of the oxygen concentration measurement cell by detecting an internal resistance of said oxygen concentration measurement cell and configured to stop current supply control for the first oxygen pumping cell during the detecting;

a heater current controller for controlling a current supply to said heater so that the temperature of the oxygen concentration measurement cell detected by the temperature detector will be a preset target temperature so that the detected internal resistance of said oxygen concentration measurement cell will be of a value corresponding to said target temperature;

wherein said first, second and third oxygen ion conducting solid electrolyte layers are laminated together so that the heater heats the second measurement chamber and then heat the first measurement chamber in a direction transverse to the first, second and third electrolyte layers, and wherein the temperature of the oxygen concentration cell is controlled to the target temperature and the temperature of the first oxygen pumping cell and the second oxygen pumping cell is controlled to a constant value.

4. The apparatus for detecting NOx concentration of claim 3, further comprising a resistor through which the second current flows, wherein the voltage being detected across the resistor is used as a NOx detection signal for an engine control unit.

* * * * *